United States Patent [19]
Mimura et al.

[11] Patent Number: 5,266,344
[45] Date of Patent: Nov. 30, 1993

[54] METHOD FOR MAKING TETRAHYDROCURCUMIN AND A SUBSTANCE CONTAINING THE ANTIOXIDATIVE SUBSTANCE TETRAHYDROCURCUMIN

[75] Inventors: Akio Mimura, Fuji; Yoshimasa Takahara, Narashino; Toshihiko Osawa, Nagoya, all of Japan

[73] Assignee: Kabushiki Kaisha Kobe Seiko Sho, Kobe, Japan

[21] Appl. No.: 616,093

[22] Filed: Nov. 20, 1990

[51] Int. Cl.$^5$ .............................................. A23D 1/06
[52] U.S. Cl. ................................. 426/546; 554/7; 568/315; 568/325
[58] Field of Search ............... 426/546; 260/398.5

[56] References Cited

U.S. PATENT DOCUMENTS 4,263,333  4/1981  Maing ................................ 426/540

FOREIGN PATENT DOCUMENTS 2-49747  2/1990  Japan .
2-51595  2/1990  Japan .

OTHER PUBLICATIONS

CA 76(25)153327f Hydrocurcumine derivatives, Miyamoto et al.
Osawa et al, J. Ag. Food Chem., vol. 33(5), 1985, pp. 777–780.
Larson, Phytochem., vol. 27(4), 1988, pp. 969–978.
Mukhopadjyay et al, Agents and Actions, vol. 12(4), 1982, pp. 508–515.

*Primary Examiner*—Carolyn Paden
*Attorney, Agent, or Firm*—Oblon, Spivak, McClelland, Maier & Neustadt

[57] ABSTRACT

The present invention relates to a novel compound tetrahydrocurcumin and a substance containing the same, which are produced from curcumin or a substance containing it as a material. This substance has characteristic properties such as strong antioxidative activity and yellowish color generated from reducing the original color of curcumin. The curcumin is being produced from a Zingiberaceae plant classified into *Curcuma longa* as a tropical product and is used for a spice and a yellow pigment for curry powder and pickles. The present invention further relates to the production method.

17 Claims, 8 Drawing Sheets

METHOD FOR MAKING TETRAHYDROCURCUMIN AND A SUBSTANCE CONTAINING THE ANTIOXIDATIVE SUBSTANCE TETRAHYDROCURCUMIN

FIELD OF THE INVENTION

The present invention relates to a novel compound tetrahydrocurcumin and a substance containing the same, which are produced from a material of curcumin or a curcumin-containing substance and which have characteristic properties such as strong antioxidative activity and yellowish color generated from reducing the original color tone of curcumin, the curcumin being produced from a Zingiberaceae plant classified into *Curcuma longa* as a tropical product and being used as a spice and a yellow pigment for curry powder, pickles and the like. The present invention further relates to a production method and the use thereof. The superior antioxidative activity thereof may be utilized in the fields of food industry, medicinal industry and cosmetic industry and the like.

PRIOR ART

Foodstuffs are produced generally from agricultural, marine and livestock products. Food materials and their products may be deteriorated through contamination and decomposition with microorganisms and chemical reactions during their stages for storage, preservation and processing, so that their values as commercial products may be decreased. Therefore, there have been developed and utilized practically a variety of food additives as well as the methods to prevent their deterioration, such as thermal treatment, deoxidizer treatment, vacuum treatment, low-temperature preservation and radiation treatment.

The most serious problem among others concerning the deterioration of food materials and products is that food components may be oxidized or peroxidized with atmospheric oxygen. Oxygen is important for organisms to maintain their lives by means of respiration. On the other hand, oxygen itself is known to be reactive enough to react with various food components to oxidize or peroxidize them, resulting not only in the reduction of their values as commercial products but also in the generation of harmful substances in them. For example, it has been reported that nutritionally essential unsaturated fatty acids such as linoleic acid and linolenic acid in foodstuffs are readily peroxidized with atmospheric oxygen, to generate carcinogenic substances such as malondialdehyde and the like along with fatty acid peroxide and reactive radicals (free radicals). It has been also reported that lipid peroxide generated from peroxidation of unsaturated fatty acid molecules in lipid modifies protein and nucleic acid in organisms by means of chemical reaction, giving harmful effects such as carcinogenicity to the organisms. [Mutagen and Toxicity, Vol.5, pp. 243 (1982); Food Packaging, Vol. 17, pp. 106 (1986)].

In order to prevent such lipid peroxidation, there have been applied some packaging techniques, including removal of oxygen in a package with a deoxidizer, vacuum packaging and packaging under nitrogen-gas replacement. Alternatively, on a basis of the background of industrial progress, synthetic antioxidants such as butylhydroxyanisole (BHA) and butylhydroxytoluene (BHT) have been generally used. However, as such synthetic antioxidants have been more commonly used, food pollution has thereby increased involving serious problems from the viewpoint of safety. Consequently, consumers have showed more intense rejection against synthetic antioxidants, and thus, the total amount of synthetic antioxidants used has decreased currently.

On the other hand, as has been described above, peroxides and carcinogens generated in animal body due to the toxic actions of oxygen have been regarded to bring about harmful effects to animal cells. Furthermore, peroxidation with oxygen have been regarded to have some relation with cell aging and its longevity (Thesis for aging through free radicals). Therefore, there has been expected so much a highly safe, naturally originated antioxidant as a substance for supporting the biological preventive mechanism against oxidation, in the art in association with food, particularly health food and nutritional food, medicinal products and cosmetics.

However, only chemically synthesized vitamin C, and vitamin E (tocopherol) extracted and purified from natural products, are practically used as naturally originated antioxidants of which the use has been greatly expected in place of synthetic antioxidants involving food pollution problems.

In order to appropriately use such naturally originated antioxidants in food, medicinal products and cosmetics, it is important to find out natural antioxidants, each of them having different properties, and utilize them under the condition that each property thereof may be advantageously exhibited.

Spices from plant origin contain various compounds with antioxidative activity. For that reason, as potent substances to preserve food, they have been added to food. (Food Packaging, Vol.19, No.1, pp.97, 1987.) But many of the spices have strong inherent flavor and color, and their utility as antioxidants have been limited thereby.

For example, curcumin which is contained in *Curcuma longa*, has antioxidative activity and has been utilized as the principal ingredient of the spice produced from *Curcuma longa*, for food preservation and stabilization. Curcumin has been known to exhibit strong antioxidative activity because it has a phenolic hydroxyl group of vitamin E and a $\beta$-diketone structure which functions as a novel-type antioxidant and which was discovered in the leafwax of eucalyptus (Journal of Agricultural and Food Chemistry, Vol.33, pp.777, 1985).

Alternatively, it is also known that curcumin is an intense yellow pigment besides it has a strong antioxidative activity (Phytochemistry, Vol.27, No.4, pp.969, 1988). Therefore, curcumin has been used as a pigment in the form of food additives, including, for example, the use in curry powder and coloring pickled radish.

The present invention relates to a routine reduction procedure of a material, curcumin from natural origin, into the reduced-form curcumin, i.e., tetrahydrocurcumin, whereby providing, in place of synthetic antioxidants, an antioxidant originated from natural products, the curcumin having conventionally been used in food as a spice, curry powder and an edible yellow pigment. Such antioxidant, i.e., tetrahydrocurcumin, has not at all been known. The antioxidant is thus novel.

PROBLEMS TO BE SOLVED BY THE INVENTION

Instead of various antioxidants in current use such as synthetic antioxidants and vitamins C and E as naturally originated antioxidants, the present invention is to provide a highly safe antioxidant by modifying a substance from natural origin, to realize its application in food, medicinal products and cosmetics.

Curcumin known as an antioxidant has a specific strong color tone, so that food and the like may be colored yellow if curcumin is applied to them. Therefore, curcumin cannot be used in food and the like which shall not be colored, even though it exhibits strong antioxidative activity. Thus, there won't be avoided such drawback that curcumin cannot be applied in a wide range.

Such substance with two properties are advantageous in that the two properties may be utilized simultaneously, but currently there are pointed out a lot of cases that the utility of the substance may be restricted in the food requiring various characteristic properties.

As to the field of antioxidants, presently, there have not been developed highly applicable antioxidants which exhibit strong antioxidative activity but without coloring potential.

MEANS TO SOLVE THE PROBLEMS

Figure 1:
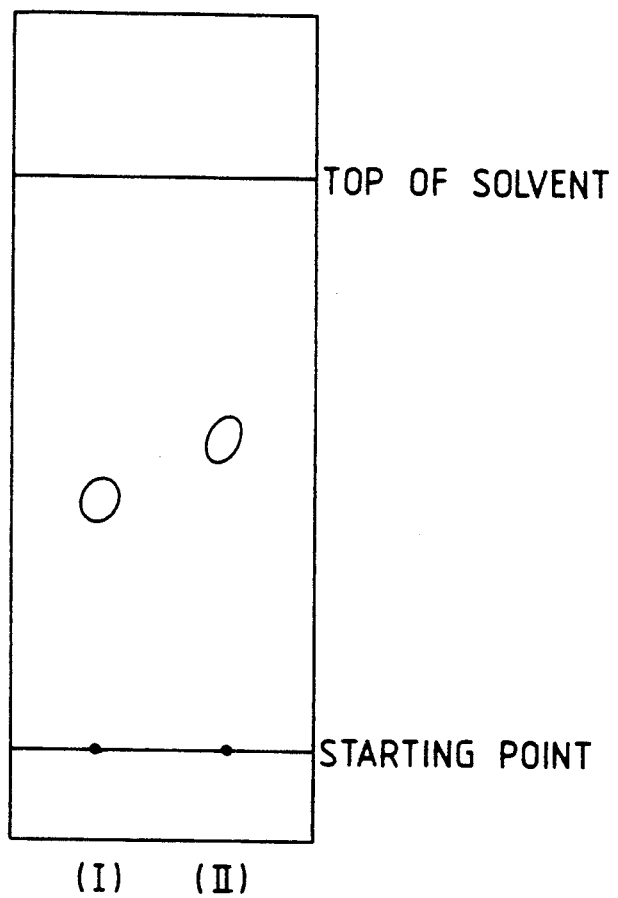
FIG. 1 is a silica gel thin-layer chromatogram. As the developer, a mixture of n-hexane and ethyl acetate at a volume ratio of 2:3 was used. Substances were detected by ultraviolet absorption. In the figure, (I) and (II) represent curcumin and tetrahydrocurcumin, respectively.

The present invention has been carried out in order to solve all these problems in view of pollution prevention and securing safety, based on the concept that industrially it may be more beneficial to utilize the useful characteristic properties of a highly safe, naturally originated substance conventionally used in food, after modification thereof, compared with the use of synthetic chemical substances.

As a result of investigations in various fields, the inventors have got an inventive idea focusing on curcumin, such that some chemical modification of curcumin may produce a novel antioxidant as an objective, the curcumin having been used as a yellow pigment conventionally in food and medicinal products and being contained as the principal agent in the genus Curcuma.

The inventors have made various attempts for a variety of chemical modifications thereof. Consequently, we have found that hydrogen-adding reaction may be effected in curcumin or a curcumin containing substance quantitatively, and that the thus obtained compound (tetrahydrocurcumin) is a novel substance, having better antioxidative activity and reduced yellowish color than curcumin itself. The present invention has been achieved after further investigations on a basis of the novel, remarkable findings.

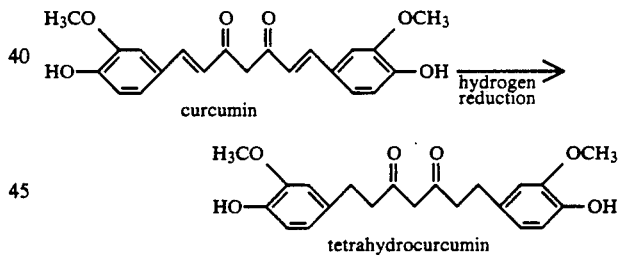

It has been found that the yellow color tone of curcumin is reduced because tetrahydrocurcumin of the present invention thus obtained by means of hydrogen reduction of curcumin, does not have double bonds. By the present property, the drawback of curcumin regarding its utility due to the strong yellow color tone thereof has been eliminated completely, which may develop a dramatic industrial aspect in its application to food additives and cosmetic additives.

More surprisingly, a phenomenon has also been found such that antioxidative activity is much more enhanced in tetrahydrocurcumin with no double bonds in its molecule than in curcumin with double bonds. It is considered that the covalent double bonds in the curcumin molecule may suppress its antioxidative activity.

It has been known that curcumin is a yellow pigment with antioxidative activity (Phytochemistry, Vol. 27, No. 4, pp. 969, 1988). Tetrahydrocurcumin to be produced by the present invention is an absolutely novel compound. The properties of tetrahydrocurcumin, as are represented by the strong antioxidative activity and the reduced yellowish color tone, have been found for the first time by the present invention.

According to the present invention, antioxidative activity was analyzed by the methods routinely used as analytical technique with similarity to biological systems, such as peroxidation of rabbit erythrocyte membrane lipid and the analysis technique by means of rat liver microsomal enzyme systems (Anti-mutagenesis and Anti-carcinogenesis Mechanism, published by Plenum Publishing Corporation, pp. 131, 1986), as well as the chemical analysis on a basis of the natural oxidation system of linoleic acid. The chemical analysis is routinely used for the research on antioxidants (Agricultural and Biological Chemistry, Vol. 45, pp. 735, 1981). Tetrahydrocurcumin to be used in the present invention showed strong antioxidative activities by any one of the above methods.

There will be now explained the method for obtaining tetrahydrocurcumin through hydrogen reduction of the material curcumin produced from Curcuma longa.

After curcumin is dissolved in an organic solvent including acetone, methanol, ethanol, etc., the double bonds in the curcumin molecule may be reduced by a hydrogen-adding catalyst, such as activated Raney-nickel catalyst routinely used in the production of food additives and a hardened oil for margarine and shortening. Any solvent may be employed other than acetone, if it may dissolve curcumin. There may be used any hydrogen-adding catalyst being used in the production of edible hardened oils, such as manganese catalysts, copper catalysts, zinc catalysts, and the like besides the reduced nickel. The condition for hydrogen reduction may be in accordance with the condition for the production of hardened oils. (Edible Oils and Fats and their Processing, pp. 74, published by Kenpakusha, 1981)

In order to recover the tetrahydrocurcumin produced through the reduction, the routine silica gel chromatography may be used. The hydrogen reduction is effected in almost quantitative manner without causing any side reactions, and thus curcumin is completely reduced into tetrahydrocurcumin. Accordingly, tetrahydrocurcumin is easily recovered.

The chemical structure of the thus obtained tetrahydrocurcumin may be identified by mass-spectrum, proton NMR and the like.

Figure 2:
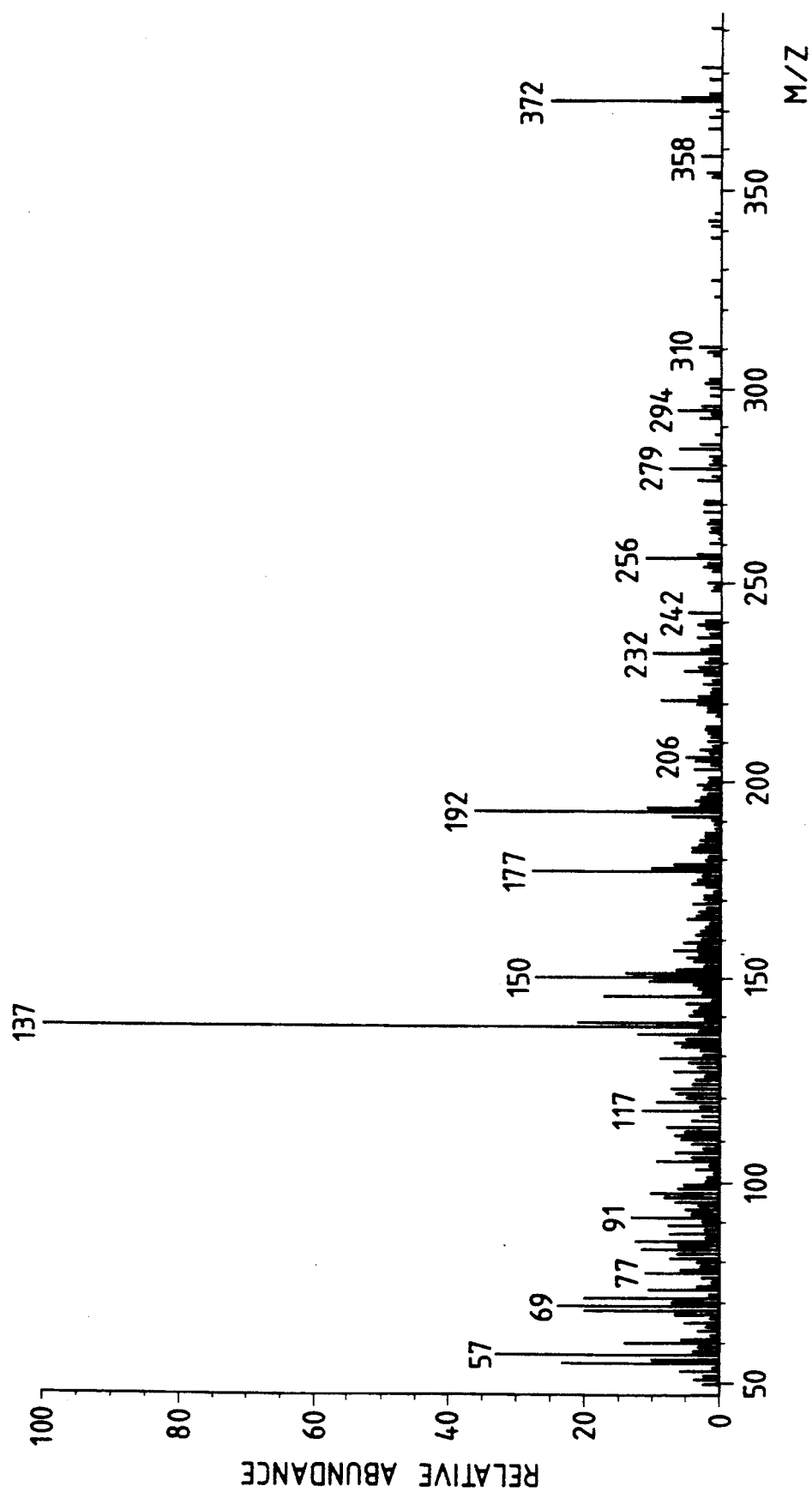
FIG. 2 is a chart representing a mass spectrum of tetrahydrocurcumin.
Figure 3:
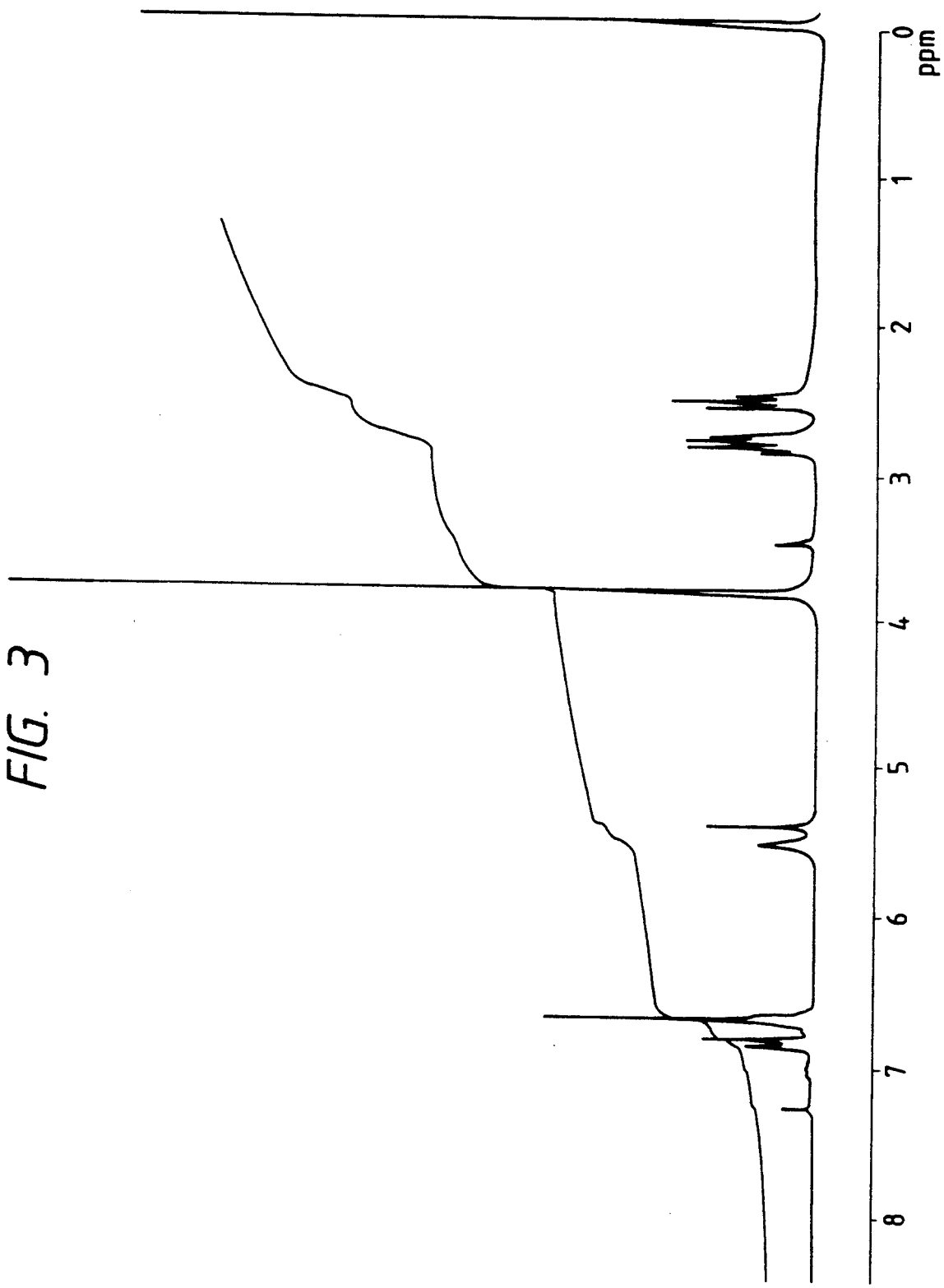
FIG. 3 is a $^1$H-NMR spectrum of tetrahydrocurcumin.

FIG. 1 is a chart developed by silica gel thin-layer chromatography. FIG. 2 is a chart representing a mass spectrum. The spectrum shows that the molecular weight of tetrahydrocurcumin is 372. FIG. 3 is a chart representing a $^1$H-NMR spectrum of tetrahydrocurcumin. The analysis of this chart demonstrates the reduction of the double bonds of curcumin. Thus, the structure of tetrahydrocurcumin was determined to have the following structure.

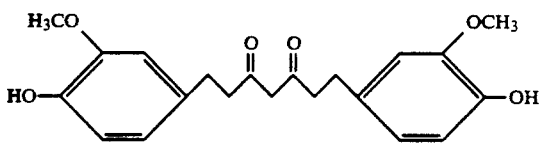

The antioxidative activity of tetrahydrocurcumin thus obtained will now be described below.

Figure 4:
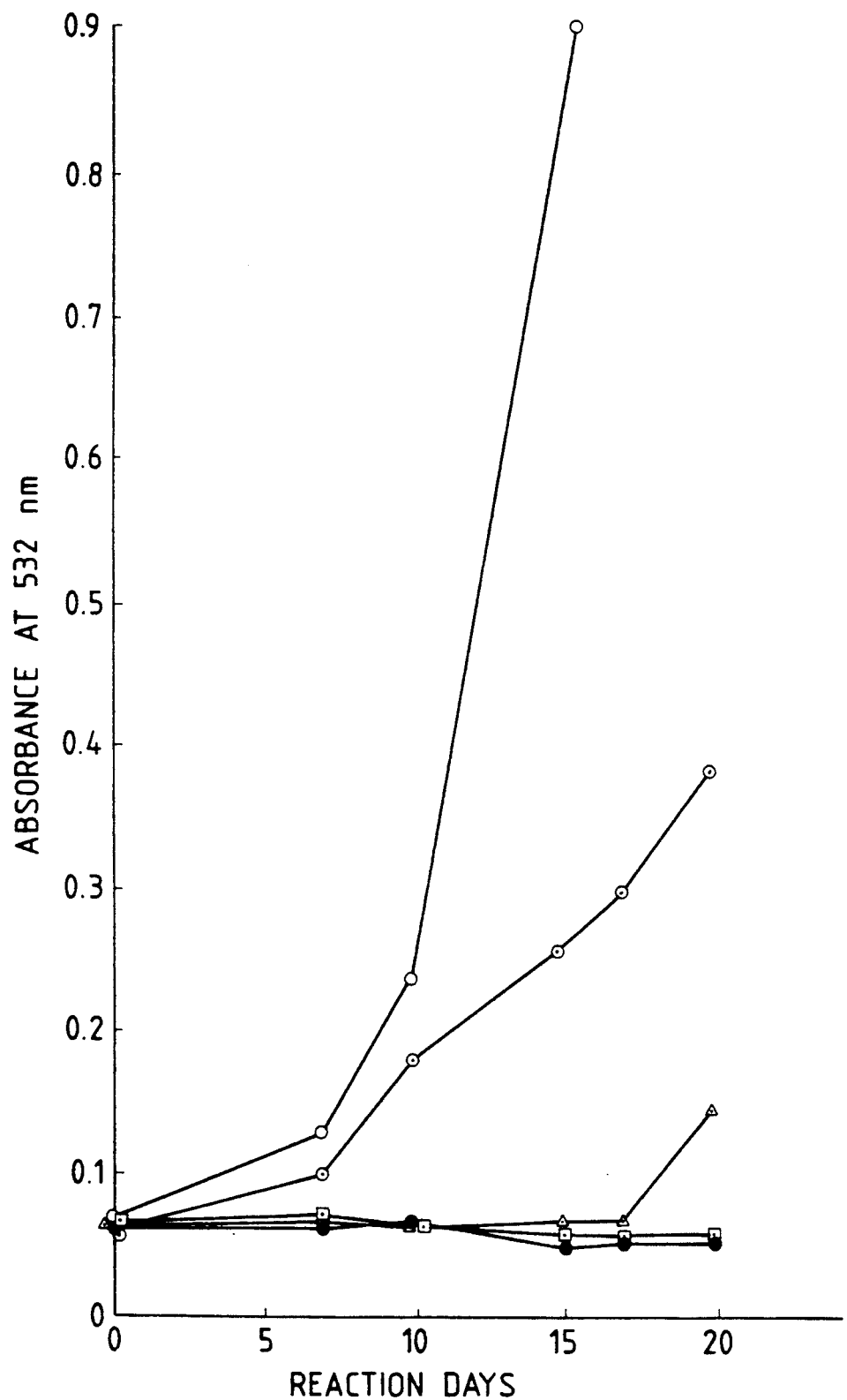
FIG. 4 shows the antioxidative activity measured by the thiobarbituric acid technique.
- ○: Control
- ●: Tetrahydrocurcumin
- ◉: Curcumin
- ▲: α-Tocopherol
- ▣: BHA.

FIG. 4 shows the antioxidative activity of tetrahydrocurcumin measured by the thiobarbituric acid technique to determine the suppression on natural oxidation of linoleic acid in atmosphere. Because the antioxidant was not added to a control group, the coloring degree of thiobarbituric acid increased. This phenomenon indicates the occurrence of natural oxidation of linoleic acid. It is observed that tetrahydrocurcumin has stronger antioxidative activity than curcumin produced from Curcuma longa or α-tocopherol.

Figure 5:
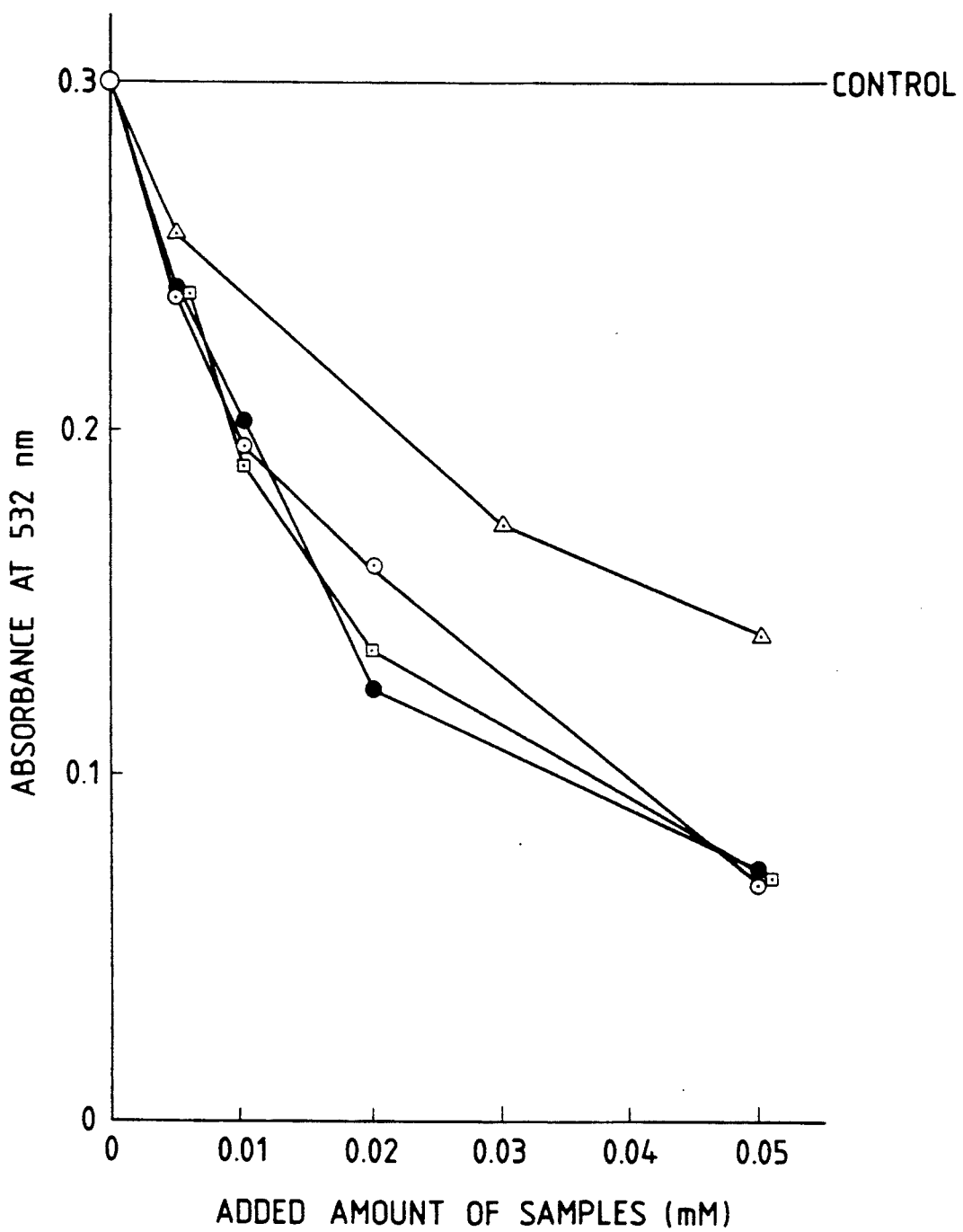
FIG. 5 shows the antioxidative activity measured by use of rabbit erythrocyte membrane lipid.
- ○: Control
- ●: Tetrahydrocurcumin
- ◉: Curcumin
- ▲: α-Tocopherol
- ▣: BHA.

FIG. 5 shows the antioxidative activity of tetrahydrocurcumin measured by the method to determine the suppression on peroxidation of rabbit erythrocyte membrane lipid, the method being currently employed as an analytical method with similarity to biological systems. It is observed that tetrahydrocurcumin has stronger antioxidative activity than t α-tocopherol.

The antioxidant according to the present invention is obtained by chemically modifying naturally originated curcumin, so it is extremely safe with the toxicity quite low almost undetectable. The antioxidant may be added and used in food and cosmetics, as it is or it is dissolved in solvents, or fats and oils, or essential oils. In some cases, curcumin is added to food, cosmetics and the like before carrying out the hydrogen additive reaction, whereby the curcumin is directly prepared into an antioxidant therein.

Furthermore, according to the present invention, curcumin as an antioxidant is mixed with natural fat or oil, and is then reduced into tetrahydrocurcumin, simultaneously with the reduction of the fat or oil by hydrogen (this process is referred to as hardening). During such process, a hardened oil in combination with tetrahydrocurcumin may be produced.

On industrial scale, the hardened oil from natural fat and oils has currently been produced practically through the hydrogen addition process, and has been supplied in a great amount as a material for margarine and shortening (Edible Oils and Fats and their Processing, published by Kenpakusha, 1981). Since the condition for industrially producing the hardened oil corresponds to the condition for producing tetrahydrocurcumin from curcumin and there is not observed any interaction between the two conditions, the natural fat and oils and the curcumin may be reduced while the two components are coexistent.

That is, curcumin is mixed and added to various fat and oils at the same time when they are placed in an apparatus for hydrogen reduction, and subsequently subjected to the routine condition for hydrogen reduction of natural fat and oils. The oxidation of the natural fat and oils may be prevented by curcumin, while the oxidation of the hardened oil thus produced may be prevented by the tetrahydrocurcumin produced simultaneously. Thus, the oxidation of the fat and oils may be thoroughly prevented.

In accordance with the present invention, an admixture of curcumin-containing curcuminoids which may be easily extracted from the root of Curcuma longa may be reduced by hydrogen, to produce an admixture of the bleached curcuminoids exerting enhanced antioxidative activity, without the separation process of the curcuminoids into individual components.

Curcuminoids are contained in the rhizoma of Curcuma longa and may be obtained at a relatively good yield by means of extraction into organic solvents. For example, the root of Curcuma longa was dewaxed with petroleum ether, extracted into benzene, concentrated and dried to give an orange powder, which contained curcumin (1) of about 50%, substance (2) of 20 to 25%, substance (3) of 20 to 25% and substance (4) of 5 to 10% (Formula I).

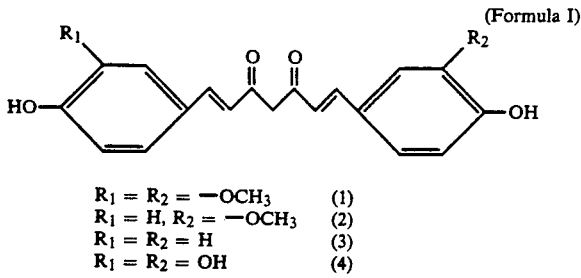

(Formula I)

R₁ = R₂ = —OCH₃ (1)
R₁ = H, R₂ = —OCH₃ (2)
R₁ = R₂ = H (3)
R₁ = R₂ = OH (4)

There will now be explained the method for obtaining the reduced-form curcuminoids from the root of *Curcuma longa* as a material.

The dried root of *Curcuma longa* in powder is extracted into petroleum ether and dewaxed, and further extracted into an organic solvent such as benzene and the like, producing the yellow extract in solution, which is concentrated and dried under reduced pressure into an orange powder, Curcumin and its similar substances contained in the powder, are referred to as curcuminoids according to the present invention, and they have structures aforementioned. The curcuminoids as dissolved in an organic solvent such as acetone, methanol, ethanol, etc. are generally used for the production of food additives and hardened oils for margarine and shortening. The double bonds in the molecules of curcuminoids may be reduced by hydrogen gas, using an activated catalyst for hydrogen addition, including the Raney-nickel catalyst. Any solvent which may dissolve curcuminoids may be used, other than acetone. There may be used any hydrogen-adding catalyst for use in the production of edible hardened oils, such as manganese catalysts, copper catalysts, zinc catalysts, and the like besides the reduced nickel. The condition for hydrogen reduction may be in accordance with the condition for the production of hardened oils (Edible Oils and Fats and their Processing, pp. 74, Kenpakusha, 1981).

The reduced-form curcuminoids thus obtained by reduction may be easily recovered. Their hydrogen reduction is effected in almost quantitative manner, so that the entire amount of curcuminoids as a material is completely reduced into the reduced-form curcuminoids. Accordingly, by removing the catalyst from the reaction solution and concentrating and drying the resulting solution, a crude product of the reduced-form curcuminoids may be obtained. The crude product may be purified by the routine silica gel chromatography and if necessary, the thus purified product may be separated into each component.

Figure 7:
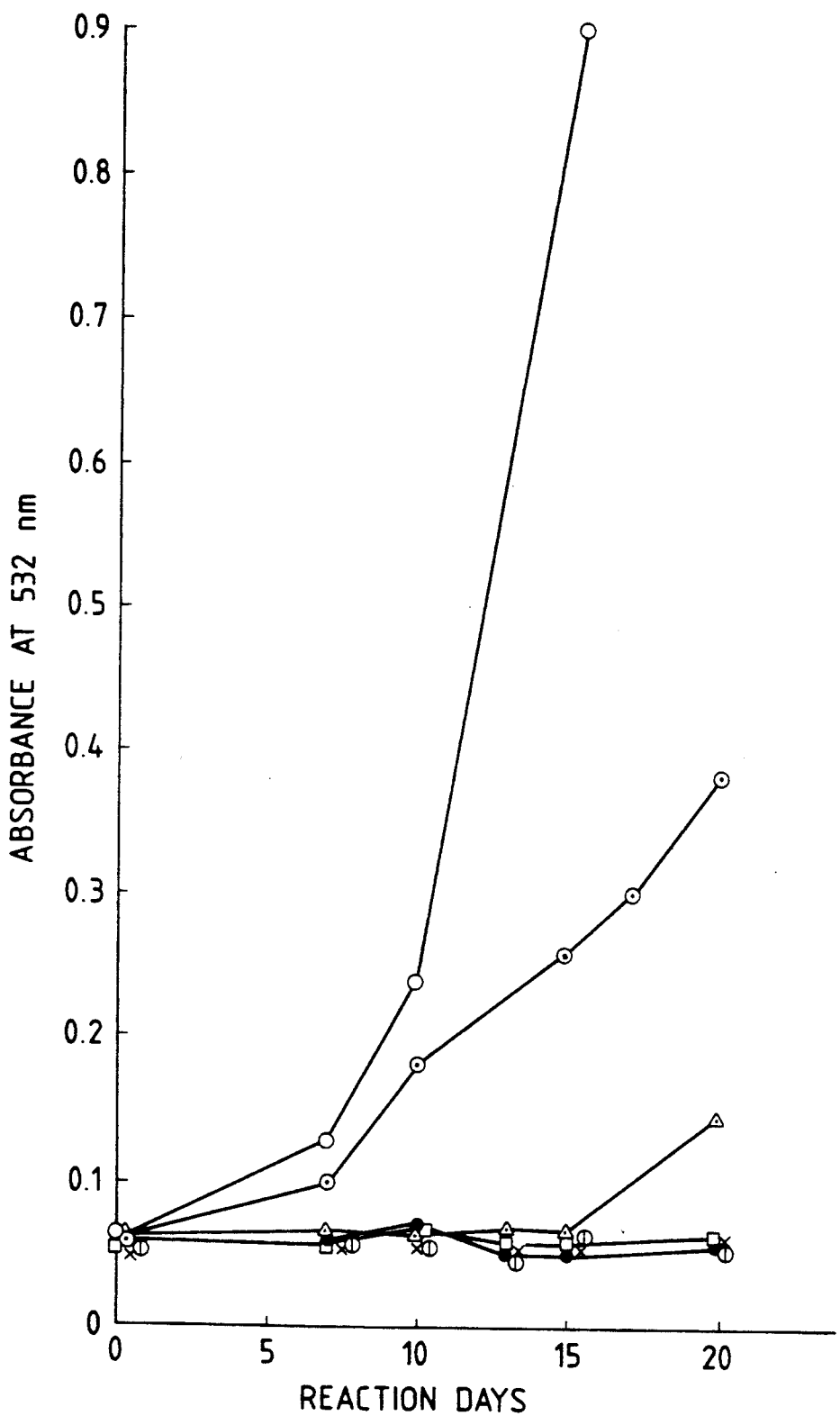
FIG. 7 shows the antioxidative activity of curcuminoids, measured by the thiobarbituric acid technique.
- ○: Control
- △: α-Tocopherol
- ●: $R_1=R_2=$—$OCH_3$ in formula (II)
- ×: $R_1=H$, $R_2=$—$OCH_3$ in formula (II)
- □: $R_1=R_2=H$ in formula (II)
- ⊕: $R_1=R_2=OH$ in formula (II)
- ◉: Curcumin.

FIG. 7 shows the antioxidative activity of the reduced-form curcuminoids measured by the thiobarbituric acid technique to determine the suppression on the natural oxidation of linoleic acid by atmospheric oxygen. Because the antioxidant was not added to a control group, the coloring degree of thiobarbituric acid increased. This phenomenon indicates the occurrence of natural oxidation of linoleic acid. It is observed that the reduced-form curcuminoids have stronger antioxidative activity than α-tocopherol.

The antioxidant according to the present invention is obtained by chemically modifying curcuminoids from natural origin, so that it is extremely safe with the toxicity quite low almost undetectable. The antioxidant may be added and used in food and cosmetics, as it is or is dissolved in solvents, or fat and oils, or essential oils. In some cases, curcuminoids and the extracts from *Curcuma longa* may be added to food, cosmetics and the like before carrying out the hydrogen additive reaction, whereby they are directly prepared into antioxidants therein.

Furthermore, the antioxidant of the present invention, is obtained by reducing curcuminoids comprising an admixture of individual components without the separation process into their individual components. Therefore, it is not required to carry out such separation process being complex and costly, so that the antioxidant may be produced economically for a short period. Additionally, as a variety of antioxidants are present in the above antioxidant of the present invention, a wide range of antioxidative activities may be obtained.

The present invention will now be explained and illustrated in Examples and Experimental Examples, but the invention may not be limited to them.

EXAMPLE 1

One gram (1.0 g) of curcumin was dissolved in 20 ml of acetone and placed in a 100-ml glass reactor for reduction, to which was then added 500 mg of activated Raney-nickel catalyst. Subsequently, the atmosphere of the reactor was replaced for hydrogen gas by the routine method. A rubber-made balloon filled with hydrogen gas was arranged on the upper portion of the reactor in order to keep hydrogen gas pressure constant in the reactor by supplying hydrogen gas to make up for the consumed amount of hydrogen gas. The reactor was stirred while maintained at a given temperature in a constant-temperature water bath kept at 30° C. for 2-hour reduction.

After completion of the reaction, the Raney-nickel catalyst was removed from the solution by filtering, which was then evaporated and dried by concentration under reduced pressure and was dissolved again in a small amount of acetone.

A glass column (2 cm diameter × 30 cm length) for chromatography was prepared by filling it with silica gel for chromatography and flowing n-hexane in it. A sample solution containing the reactant was applied on the column and adsorbed on the silica gel, which was then eluted by a mixed solvent of n-hexane and ethyl acetate. Tetrahydrocurcumin as the reactant was eluted by the mixed solvent containing ethyl acetate at a volume ratio of 40 to 50%, and was then collected. Subsequently, the eluate was concentrated and dried under reduced pressure to obtain 674 mg of tetrahydrocurcumin. It was identified by analytical silica gel thin-layer chromatography that this was a purified product.

EXPERIMENTAL EXAMPLE 1

Tetrahydrocurcumin isolated and refined to its purified state in Example 1 was used as a sample, while curcumin, BHA as a synthetic antioxidant, and α-tocopherol as a natural oxidant were used as comparative substances, in order to compare their antioxidative activities.

The thiobarbituric acid technique is generally employed for measuring antioxidative activity and its principle will be briefly explained hereinafter.

Using linoleic acid of an unsaturated fatty acid, as a substrate, and atmospheric oxygen as an oxidant, substances which are responsive to thiobarbituric acid and are generated by auto-oxidation of linoleic acid are measured. The substances from auto-oxidation of linoleic acid react with thiobarbituric acid to produce a red pigment, which absorbance at 532 nm is measured to determine the amount of linoleic acid through auto-oxidation. The antioxidative activity is determined from the degree of suppression of such system on the auto-oxidation of linoleic acid.

The antioxidative activity of a sample obtained in the present invention was determined in such manner and shown in FIG. 4. Each sample of 200 μg was added to 20 ml of each reaction solution.

Tetrahydrocurcumin greatly suppressed the oxidation of linoleic acid for 20-day auto-oxidation.

EXAMPLE 2

One hundred grams (100 g) of beef fat was placed in a glass reaction apparatus for hydrogen addition, to which were then added the activated Raney-nickel catalyst containing 0.5 g of nickle and 1 g of curcumin produced from *Curcuma longa*. The reaction apparatus was a 500-ml capacity and equipped with a stirring shaft through its upper portion to mix the contents in the reaction apparatus. On the other hand, a rubber-made balloon arranged on the upper portion of the reaction apparatus was filled with hydrogen gas. The pressure inside the reaction apparatus was kept at approximately normal pressure, by supplying hydrogen gas to make up for the consumed amount of the gas. After the atmosphere inside the reaction apparatus was completely replaced for hydrogen gas, the reaction temperature was maintained at 180° C. in an oil bath for 2-hour reaction. At the initial reaction stage, the yellow color tone of curcumin was still observed in the reaction mixture. But the yellow color tone gradually reduced as the reaction proceeded.

After completion of the reaction, the beef fat was taken out from the reaction apparatus and subjected to the analysis for characterizing the hardened oil produced. The melting point was 53° C. and the iodine number was 23. The beef fat used as a material showed a melting point of 44° C. and an iodine number of 37.

After completion of the reaction, 5 g of the beef fat was taken out, to which was added 100 ml of acetone to extract the tetrahydrocurcumin produced by the reaction. The extract was separated from the solid by filtering, and then an oily product was obtained after evaporating acetone. This was subjected to silica gel chromatography (a silica gel chromatocolumn of 2 cm diameter ×30 cm length) to isolate tetrahydrocurcumin. The extract was applied on the silica gel column, which was then eluted sequentially by n-hexane and a mixed solvent of n-hexane and ethyl acetate. The fractions eluted by the mixed solvent containing ethyl acetate at a ratio of 40 to 50% were collected and subsequently, were concentrated and dried under reduced pressure. This dried product was dissolved in a small amount of acetone and subjected to routine analytical thin-layer chromatography. It was developed and quantified. The reaction yield of tetrahydrocurcumin was 77%.

EXPERIMENTAL EXAMPLE 2

The antioxidative activity of the hydrogen-added beef fat obtained in Example 2 containing tetrahydrocurcumin was measured by the thiobarbituric acid technique routinely used. As comparative samples, a synthetic antioxidant BHA and a natural antioxidant α-tocopherol were used.

The thiobarbituric acid technique is generally employed for measuring antioxidative activity and its principle will be briefly explained hereinafter.

Using linoleic acid, an unsaturated fatty acid, as a substrate, and atmospheric oxygen as an oxidant, substances which are responsive to thiobarbituric acid and are generated by auto-oxidation of linoleic acid are measured. The substances from auto-oxidation of linoleic acid react with thiobarbituric acid to produce a red pigment, which absorbance at 532 nm is measured to determine the amount of linoleic acid through auto-oxidation. The antioxidative activity is determined from the degree of suppression of such system on the auto-oxidation of linoleic acid.

Figure 6:
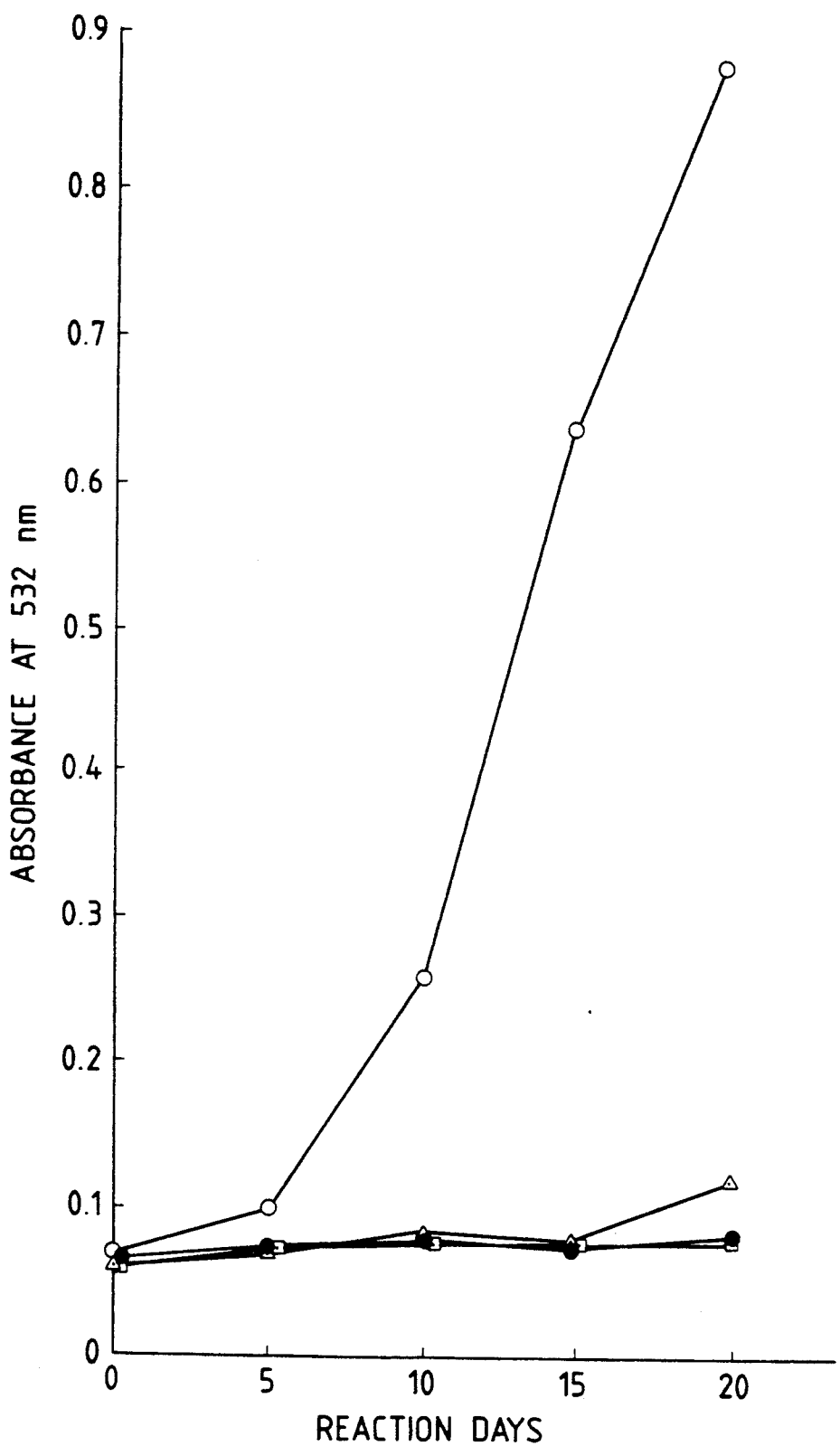
FIG. 6 shows the antioxidative activity of a hardened oil, measured by the thiobarbituric acid technique.
- ○: Control
- ●: Hardened oil
- ▲: α-Tocopherol
- ▣: BHA.

The antioxidative activity of a sample obtained in the present invention was determined in such manner and shown in FIG. 6. To 20 ml of each reaction solution was added 1 mg of the hardened fat and oils or other each sample of 200 μg. The results show that the hardened oil has strong antioxidative activity originated from tetrahydrocurcumin.

EXAMPLE 3

One kilogram (1 kg) of the dry powder of the root of *Curcuma longa* was soaked in 2 l of petroleum ether and extracted overnight under intermittent stirring. This was filtered to yield a dewaxed powder. Subsequently, 2 l of benzene was added to the powder and then subjected to the same procedure for extraction. After filtering, there was obtained a yellow extract which was then concentrated and dried under reduced pressure to obtain an orange dry powder of 13 g. This was analyzed by liquid chromatography generally used for separation and analysis. It was determined that this contained 8.3 g of curcuminoids represented by formula (I).

One gram (1 g) of the thus obtained curcuminoids was dissolved in 20 ml of acetone and placed in a 100-ml glass reactor for reduction, to which was then added 500 mg of activated Raney-nickel catalyst. Subsequently, the atmosphere of the reactor was replaced for hydrogen gas by the routine method. A rubber-made balloon filled with hydrogen gas was arranged on the upper portion of the reactor in order to keep hydrogen gas pressure constant in the reactor, by supplying hydrogen gas to make up for the consumed amount of gas. The reactor was stirred while maintained at a given temperature in a constant-temperature water bath kept at 30° C., for 2-hour reduction.

After completion of the reaction, the Raney-nickel catalyst was removed by filtering from the solution, which was then evaporated and dried by concentration under reduced pressure and was dissolved again in a small amount of acetone.

A glass column (2 cm diameter×30 cm length) for chromatography was prepared by filling it with silica gel for chromatography and flowing n-hexane into it. A sample solution containing the reactant was applied on the column and absorbed on the silica gel, which was then eluted by a mixed solvent of n-hexane and ethyl acetate. Reduced curcuminoids were eluted by the mixed solvent containing ethyl acetate at a volume ratio of 30 to 60% and were collected. Subsequently, the eluate was concentrated and dried under reduced pressure to obtain 714 mg of reduced curcuminoids.

It was identified by analytical thin-layer chromatography on a silica gel column that this was a mixture of the reduced-form curcuminoids.

EXPERIMENTAL EXAMPLE 3

The reduced-form curcuminoids mixture prepared in Example 3 was used as a sample, while curcumine, a synthetic antioxidant BHA and a natural antioxidant α-tocopherol were used as comparative substances, in order to compare their antioxidative activities.

The thiobarbituric acid technique is generally employed for measuring antioxidative activity and its principle will be briefly explained hereinafter.

Using linoleic acid, an unsaturated fatty acid, as a substrate, and atmospheric oxygen as an oxidant, the measurement of the substances which are responsive to thiobarbituric acid and are generated by auto-oxidation of linoleic acid is carried out. The substances from auto-oxidation of linoleic acid react with thiobarbituric acid to produce a red pigment, which absorbance at 532 nm is measured to determine the amount of linoleic acid through auto-oxidation. The antioxidative activity is determined from the degree of suppression of such system on the auto-oxidation of linoleic acid.

Figure 8:
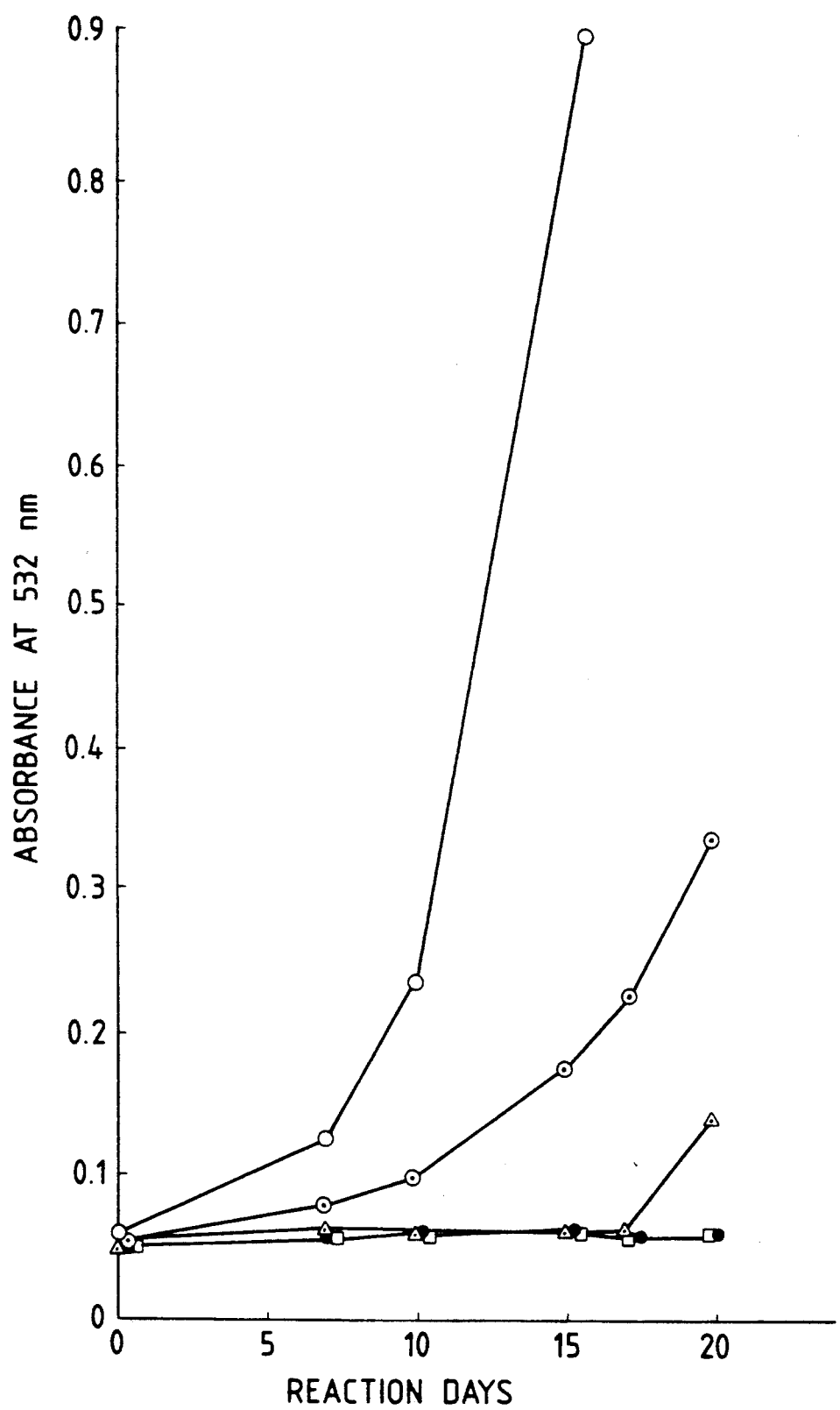
FIG. 8 shows the antioxidative activity of a curcuminoids mixture, measured by the thiobarbituric acid technique.
- ○: Control
- ◉: Orange powder produced after concentration and drying of an extract from Curcuma longa
- ▲: α-Tocopherol
- ●: A mixture of reduced-form curcuminoids
- □: BHA.

The antioxidative activity of the samples obtained in the present invention was determined in such manner and shown in FIG. 8. Each sample of 200 μg was added to 20 ml of each reaction solution.

As is shown in the figure, the reduced-form curcuminoids greatly suppressed the oxidation of linoleic acid for 20-day auto-oxidation.

What is claimed is:

1. Method for producing tetrahydrocurcumin, comprising reducing curcumin by a metallic catalyst in the presence of hydrogen in an organic solvent.

2. The method of claim 1, wherein said metallic catalyst is selected from the group consisting of Raney nickel, manganese catalysts, copper catalysts and zinc catalysts.

3. The method of claim 2, wherein said metallic catalyst is Raney nickel.

4. The method of claim 2, wherein said hydrogen is hydrogen gas.

5. The method of claim 1, wherein said solvent is selected from the group consisting of acetone, methanol and ethanol.

6. Hardened oil containing tetrahydrocurcumin.

7. The hardened oil of claim 6, further containing beef fat, margarine or shortening.

8. Method for producing a hardened oil containing tetrahydrocurcumin, comprising the steps of adding curcumin to fat or oil and reducing the fat or oil by hydrogen, thereby the curcumin being simultaneously changed into tetrahydrocurcumin by hydrogenation.

9. The method of claim 8, wherein said reducing step is conducted with hydrogen gas and a catalyst selected from the group consisting of Raney nickel, manganese catalysts, copper catalysts and zinc catalysts.

10. The method of claim 9, wherein said metallic catalyst is Raney nickel.

11. Method for producing reduced-form curcuminoids, comprising the steps of extracting the root of *Curcuma longa* into a first organic solvent, and reducing the obtained extract by a metallic catalyst in the presence of hydrogen in a second organic solvent.

12. The method of claim 11, wherein said metallic catalyst is selected from the group consisting of Raney nickel, manganese catalysts, copper catalysts and zinc catalysts.

13. The method of claim 12, wherein said metallic catalyst is Raney nickel.

14. The method of claim 12, wherein said hydrogen is hydrogen gas.

15. The method of claim 11, wherein said first organic solvent is benzene, and said second organic solvent is selected from the group consisting of acetone, methanol and ethanol.

16. The method of claim 11, wherein said reducing step is conducted with hydrogen gas and a catalyst selected from the group consisting of Raney nickel, manganese catalysts, copper catalysts and zinc catalysts.

17. Method for producing reduced-form curcuminoids, comprising reducing curcuminoids by a metallic catalyst in the presence of hydrogen in an organic solvent.

* * * * *